United States Patent [19]
Goldstein

[11] Patent Number: 5,736,322
[45] Date of Patent: *Apr. 7, 1998

[54] SYNTHETIC ORAL FLUID STANDARD

[75] Inventor: Andrew S. Goldstein, Portland, Oreg.

[73] Assignee: Epitope, Inc., Beaverton, Oreg.

[*] Notice: The portion of the term of this patent subsequent to Jun. 7, 2015, has been disclaimed.

[21] Appl. No.: 608,431

[22] Filed: Feb. 28, 1996

Related U.S. Application Data

[63] Continuation-in-part of Ser. No. 480,790, Jun. 7, 1995.

[51] Int. Cl.$^6$ ............... C12Q 1/70; A61K 38/47; A61K 7/28; A01N 59/08
[52] U.S. Cl. ............... 435/5; 424/94.61; 424/50; 424/680; 514/780
[58] Field of Search ............... 435/5; 424/94.61, 424/50, 680; 514/780

[56] References Cited

U.S. PATENT DOCUMENTS

| | | | |
|---|---|---|---|
| 5,103,836 | 4/1992 | Goldstein et al. | 128/760 |
| 5,335,673 | 8/1994 | Goldstein et al. | 128/760 |
| 5,339,829 | 8/1994 | Thieme et al. | 128/760 |
| 5,494,665 | 2/1996 | Saito et al. | 424/94.61 |

FOREIGN PATENT DOCUMENTS

| | | | |
|---|---|---|---|
| WOA94 04078 | 3/1994 | WIPO | A61B 10/00 |
| WOA95 27205 | 3/1994 | WIPO | G01N 33/52 |

OTHER PUBLICATIONS

Int. J. Biochem. (1993), 25(5), 681–7 Coden: IJBOB-V;ISSN: 0020–711X, XP002015116 Slomiany, B.L. et al.: "Control of mucin molecular forms expression by salivary protease: differences with caries".

*Physicians' Desk Reference*, pp. 1211, 1378–1379.

*Journal of Oral Pathology*, 1983, 12:336–341 "Remineralization of Softened Human Enamel In Mucin– or CMC–Containing Artificial Salivas", T.B.F.M. Gelhard et al.

*Human Saliva: Clinical Chemistry and Microbiology*, vol. 1, Jorma O. Tenovuo et al., pp. 77–95.

*Clinical and Diagnostic Virology* 2 (1994) 231–243, "Detection of Antibody to HIV in Saliva: A Brief Review", Philip P. Mortimer et al.

*Primary Examiner*—Lynette F. Smith
*Assistant Examiner*—Brett L. Nelson
*Attorney, Agent, or Firm*—Townsend and Townsend and Crew LLP

[57] ABSTRACT

A substitute oral fluid standard for testing, calibration, and standardization of devices and methods for collection, storage, and analysis of oral fluids. The oral fluid standard comprises a mucin and a protease inhibitor.

36 Claims, No Drawings

SYNTHETIC ORAL FLUID STANDARD

This is a continuation in part of U.S. Ser. No. 08/480,790, filed on Jun. 7, 1995, which is herein incorporated by reference for all purposes.

BACKGROUND OF THE INVENTION

Numerous analytical methods have been developed for determining the presence or absence and/or quantifying the amount of various analytes in tissues and fluids of organisms. Currently most diagnostic testing is done with either blood, urine, fecal material, or tissue biopsy. Testing based on these materials, however, entails substantial invasion of privacy and poses a significant safety hazard (particularly with testing of blood). In contrast, the collection of oral fluid including saliva and/or mucosal transudate for testing entails relatively little invasion of privacy, is relatively safe, and can be accomplished rapidly with relative ease.

The idea for using oral fluid in a detection method has been discussed in scientific and clinical research for some time. A multitude of researchers have investigated using oral fluid as a possible clinical specimen for diagnosis of specific disease states or altered metabolic activity (see e.g., *Annl. New York Acad. Sci.*, Vol. 694: *Saliva as a Diagnostic Fluid*, Malamud and Tabak, eds., N.Y. Acad. Sci. Pub. (1993)). There is a preponderance of evidence that suggests that oral fluids might be extremely useful samples for the detection of certain analytes. The basic technological premise is that analytes present in blood will pass through the oral mucosa and/or salivary glands into the oral cavity where they can be detected. Further it is assumed that the concentration of analyte in oral fluid will be indicative of the blood concentration. There is thus considerable interest in the development of devices for the collection, transport, and sample handling of oral fluids and in the development of oral fluid-based assays; in particular assays for various antibodies and metabolites.

In contrast to blood and urine for which there exist standard devices for the collection, transport, preservation, handling and detection, there are no apparent standard devices or assays for oral fluids. Development of oral fluid-based diagnostics, metabolite assays and associated collection, handling, storage and preservation systems requires testing of such assays and systems under carefully controlled circumstances. Similarly the Food and Drug Administration (FDA) approval process also requires rigorous testing and even routine manufacturing of collection devices and assays requires periodic testing for quality assurance and control.

Such testing requires large quantities of oral fluid. Oral fluid, human or otherwise is difficult and expensive to obtain in large quantity. In addition, the characteristics of the oral fluid vary between sources, or even with time (e.g., time after feeding) in a single source. Thus, naturally occurring oral fluid does not provide a fully satisfactory fluid for development and testing of oral fluid-based diagnostic methods and apparatus.

SUMMARY OF THE INVENTION

This invention provides synthetic oral fluid standards suitable for use in the development, approval, and production of oral fluid-based diagnostics and metabolite assays and associated collection, handling, storage and preservation systems. The synthetic oral fluids of this invention act as suitable surrogates, in this context, for naturally produced oral fluids (e.g. salivas and mucosal transudates).

In a preferred embodiment, the oral fluid standards of this invention comprise an aqueous solution of a mucin and a protease inhibitor. Even more preferred oral fluid standards additionally include an amylase. Any protease inhibitor that reduces or eliminates proteolytic activity associated with a mucin is suitable. Preferred protease inhibitors inhibit the papain-like (cysteine) proteases. Particularly preferred protease inhibitors include, but are not limited to, leupeptin, antipain, benzamidine, chymostatin, pepstatin A, and aprotinin. In a particularly preferred embodiment, the mucin is present at a concentration ranging from about 0.001% to about 0.4% (w/v), the amylase is present at a concentration ranging from about 0.1 g/L to about 5.0 g/L and the protease inhibitor is present in a concentration sufficient to reduce or prevent proteolysis of antibodies added to the oral fluid standard.

The oral fluid standards can additionally include one or more components selected from the group consisting of magnesium, calcium, sodium, phosphate, chloride, potassium, and bicarbonate. The oral fluid standard can additionally include a preservative most preferably a preservative selected from the group consisting of thimerosal, gentamycin, chlorhexidine digluconate, and polyhexamethylenediguanide.

The oral fluid standards can additionally include one or more analytes. Suitable analytes include, but are not limited to an antibody selected from the group consisting of an antibody to HIV-1, an antibody to HIV-2, an antibody to HTLV-1, an antibody to HTLV-2, an antibody to *Helicobacter pylori*, an antibody to hepatitis A, an antibody to hepatitis B, an antibody to hepatitis C, an antibody to measles, an antibody to mumps, an antibody to rubella, cotinine, cocaine, benzoylecgonine, benzodiazapine, tetrahydrocannabinol, theophylline, phenytoin, β-hCG, thyroxine, thyroid stimulating hormone, follicle stimulating hormone, luteinizing hormone, glucose, insulin, or cholesterol.

Similarly, the standard can include serum, more preferably human serum. The serum can be positive or negative for an analyte including, but not limited to any of the above-identified analytes. A particularly preferred oral fluid standard includes nitrite at a concentration ranging from about 0.1 mM to about 2 mM; magnesium at a concentration ranging from about 0.03 mM to about 0.6 mM; calcium at a concentration ranging from about 0.5 mM to about 5.0 mM; sodium at a concentration ranging from about 2 mM to about 80 mM; phosphate at a concentration ranging from about 1.8 mM to about 25 mM; chloride at a concentration ranging from about 10 mM to about 56 mM; potassium at a concentration ranging from about 10 mM to about 40 mM; and bicarbonate at a concentration ranging from about 2 mM to about 35 mM. This standard can additionally include a preservative. An even more preferred standard includes about 0.01 g/L $NaNO_2$; about 0.03 g/L $MgCl_2$; about 0.21 g/L $CaCl_2.2H_2O$; about 0.61 g/L NaCl; about 1.63 g/L $KH_2PO_4$; about 1.00 g/L KCl; about 0.25 g/L $NaHCO_3$; about 0.20 g/L thimerosal; about 0.725 g/L amylase; about 2.0 ml 5 % mucin; and about 0.05 g/L antipain.

In still yet another embodiment, this invention provides method of testing (e.g., quality control testing) an assay for the detection of analytes in oral fluid. The method involves providing any of the above-described oral fluid standards including an analyte and performing the assay to detect and/or quantify the analyte in the oral fluid standard. The detection and/or quantification of the analyte can involve measuring the ability of the assay to detect and/or quantify the analyte in an oral fluid standard positive for the analyte as compared to an oral fluid standard negative for that analyte or as compared to natural oral fluid. The assay, as used in this context, can refer simply to a method of collecting oral fluid, or to a method of collecting and/or handling and/or storing and/or preserving oral fluid. The assay can also refer to the actual detection method (e.g., RIA, ELISA, etc.) alone, or in combination with collection, handling, storing, or preserving the oral fluid.

Definitions

The term "oral fluid standard" is used herein to refer to an aqueous solution useful as a surrogate for naturally occurring oral fluid in the testing, calibration and standardization of oral fluid collection methods and devices, oral fluid handling, preservation and storage methods and devices, and oral fluid-based assay methods and devices. Oral fluid standards are not intended as an in vivo therapeutic replacement or supplement for saliva, but rather are used as ex vivo testing standards. It will be recognized that the term oral fluid standard can refer to the oral fluid surrogate composition alone, or can refer to the oral fluid surrogate spiked with one or more additional components such as an analyte and/or human serum. The particular meaning of the term oral fluid standard will be apparent from context in which it is used.

The term "oral fluid", as used herein, refers to one or more fluids found in the oral cavity individually or in combination. These include, but are not limited to saliva and mucosal transudate. It is recognized that oral fluids (e.g., saliva) are a combination of secretions from a number of sources (e.g., parotid, submandibular, sublingual, accessory glands, gingival mucosa and buccal mucosa) and the term oral fluid includes the secretion of each of these sources individually or in combination.

The term "preservative", as used herein, is intended to designate a substance showing antimicrobial properties, in particular bactericidal properties and preferably also antifungal properties.

The term "mucins", or "mucoproteins", as used herein, refers to acid mucopolysaccharides complexed with proteins. The acid mucopolysaccharides are a group of related herteropolysaccharides usually containing two types of alternating monosaccharide units of which at least one has an acidic group (typically either a carboxyl or a sulfuric group). The terms "buccal and gastrointestinal mucins" are intended to designate any mucin which is present in the oral cavity or in the gastrointestinal system, respectively. Typical examples are mucins from salivary glands and gastric mucins.

The term "target analyte" is used herein to refer to an analyte that a particular assay (e.g., an oral fluid-based assay) is designed to detect and/or quantify. The target analyte is usually spiked into the oral fluid standard, often at a known (predetermined) concentration. The target analyte may be spiked into the oral fluid standard alone, or as a component in a mixture (e.g., human serum).

The phrase "specifically binds" when referring to a an antibody refers to a binding reaction which is determinative of the presence of the molecule for which the antibody is specific in a heterogeneous population of proteins and other biologics. Thus, under designated conditions (e.g., immunoassay conditions), the specified antibody binds to its particular "target" molecule and does not bind in a significant amount to other molecules present in the sample or to other molecules to which the antibody may come in contact in an organism.

DETAILED DESCRIPTION

This invention provides synthetic oral fluid standards suitable for use in the development, approval, production, and use of oral fluid-based diagnostics, metabolite assays and associated collection, handling, storage and preservation systems. The synthetic oral fluids of this invention act as suitable surrogates for naturally produced oral fluid while maintaining fundamental oral fluid characteristics (e.g., viscosity, pH, electrolytes) that can impact the performance (e.g., sensitivity, reproducibility, and ease of use) of oral fluid collection methods and oral fluid-based diagnostics. The synthetic oral fluid standards of this invention permit production of an "oral fluid" in greater volume (effectively limitless) and with greater homogeneity than natural oral fluids collected from organisms. The extreme homogeneity affords highly reproducible testing and evaluation of collection methods and diagnostics thus facilitating oral fluid collection system and assay development and providing a highly reproducible mechanism for ongoing quality control during the commercial manufacture of oral fluid collection systems and assays.

In addition, the composition of the synthetic oral fluid standards of this invention can be systematically altered to reflect variations in oral fluid properties (e.g., viscosity) characteristic of various pathologies (e.g., Sjögren's syndrome, salivary gland infections, cystic fibrosis, endocrine disturbances, and the like). This permits evaluation of the performance of collection systems and assays under pathological conditions.

Oral Fluid Standard Composition

In one embodiment, the synthetic oral fluid standards of this invention comprise an aqueous solution of a mucin, more preferably an aqueous solution of a mucin and a protease inhibitor, and in a most preferred embodiment the oral fluid standards comprise a aqueous solution of a mucin, a protease inhibitor, and an amylase.

The mucin is provided to approximate the viscosity and surface wetting properties of oral fluid. Mucins are glycoproteins; the chief constituent of mucus, the slimy secretions of tissues, organs and organisms, and contribute significantly to the viscosity and surface-wetting properties of oral fluid. Mucins are characteristically soluble in water, and precipitated by alcohol and acid.

Mucins used in this invention can be derived from a wide variety of "natural" sources including, but not limited to porcines, bovines, goats, sheep, cattle, felines, non-human primates, humans, and the like. Alternatively, mucins can be chemically prepared. Preferred mucins, however, are derived from non-human mammals and particularly preferred mucins are selected from the group consisting of buccal and gastrointestinal mucins. The term buccal and gastrointestinal mucins are intended to designate any mucin which is present in the oral cavity or in the gastrointestinal system, respectively. Typical examples are mucins from salivary glands and gastric mucins.

The mucin concentration is selected to reflect the mucin concentration of, and hence to achieve a viscosity similar to, the naturally occurring oral fluid(s) for which the oral fluid standard stands as a surrogate. Thus, in pathological conditions where oral fluid viscosity is abnormal, the mucin concentration of the oral fluid standard will be adjusted to approximate the viscosity of the abnormal oral fluid to provide a standard for testing methods and devices used in the pathological patient. Conversely, where oral fluid viscosity is "normal", mucin concentrations of the oral fluid standard will be adjusted to reflect normal oral fluid viscosity.

In a preferred embodiment, the mucin concentration of the oral fluid standards of this invention will range from about 0.001% to about 0.4%, more preferably from about 0.005% to about 0.2%, and most preferably from about 0.008% to about 0.1% (w/v). In one particularly preferred embodiment, the mucin concentration will be about 0.01% (w/v).

Mucins can be obtained from commercial sources (e.g. Sigma Chemical Co., St. Louis, Mo., USA)) or, as indicated above, isolated directly from various non-human mammals. Methods of isolating mucins are well known to those of skill in the art. For example, porcine gastric mucin is typically obtained as a by-product in the production of pepsin from hog stomachs. The mucin can be additionally purified by multiple alcohol precipitations, such as 2-3 precipitations with 60% ethanol. During the precipitations, and during the manipulation of the mucin, the use of gentle conditions will result in minimizing of viscosity-decreasing degradation. Alcohol precipitations are typically performed to such an extent that the mucin is substantially free of any peptone content.

The isolated mucin can be dried for storage as by spray-drying, shelf-drying, or freeze-drying. Spray-drying should be performed under conditions which are non-severe, a typical example of a preferred air inlet temperature being in the range of about 150° C. to about 240° C., typically around about 200° C., and the outlet temperature being in the range of about 90° C. to about 180° C., typically about 150° C. Similarly, methods for isolating bovine salivary mucin are described by Gravenmade et al,. *Int. J. Oral Surg.,* 3:435–439 (1974).

Mucins from different sources can be combined to form the oral fluid standard solutions of this invention. It is noted that a composition which contains porcine gastric mucin and bovine salivary mucin in a proportion of 99:1 will show properties very close to natural oral fluid with respect to surface tension and the relationship between polar and non-polar properties. Similarly, it has been found that a solution containing 4 % of porcine gastric mucin and 0.1% of bovine salivary mucin has a proportion between polar and non-polar components corresponding to about equally pronounced polar and non-polar properties, which has also been found to be the balance prevailing under natural conditions in the oral mucosa (see U.S. Pat. No. 4,438,100).

The oral fluid standards of this invention can also include other viscosity-building constituents such as carboxymethylcellulose, hydroxymethylcellulose, dextrins, polysaccharides, starches, and the like. Where additional viscosity-building constituents are included, the mucin concentration can be proportionally decreased.

It was a surprising discovery of this invention that commercially available solutions of mucins, particularly gastric and buccal mucins frequently have proteolytic activity and tend to degrade proteinaceous components in mucin solutions. It is also a discovery of this invention that protease inhibitors can be incorporated into an oral fluid standard without significantly altering properties (e.g., viscosity, ionic composition) that may effect the suitability of the synthetic oral fluid as a testing standard, and the inclusion of protease inhibitors substantially eliminates proteolytic activity. Thus, as indicated above, in a preferred embodiment, the oral fluid standards of this invention also include a protease inhibitor.

Suitable protease inhibitors can readily be determined by spiking the oral fluid standard with a protein (e.g., an antibody) and the protease inhibitor in question and monitoring the degradation (e.g., loss of binding activity) of the protein. Suitable protease inhibitors significantly reduce or eliminate degradation (hydrolysis) of the spiked protein (e.g., target analyte). Methods of assaying the binding activity of an antibody (e.g., ELISA) are well known to those of skill in the art (see, e.g., *Methods in Cell Biology* Volume 37: *Antibodies in Cell Biology*, Asai, ed. Academic Press, Inc. New York (1993); and *Basic and Clinical Immunology* 7th Edition, Stiles & Terre's (1991)).

Appropriate protease inhibitors include, any inhibitors that significantly reduce or eliminate degradation of the target analyte. Particularly preferred protease inhibitors inhibit papain-like (cysteine) proteases. Such protease inhibitors include, but are not limited to leupeptin, amastatin, PMSF, antipain, benzamidine, chymostatin, pepstatin A, and aprotinin.

Protease inhibitors are preferably present at a concentration sufficient to prevent proteolytic degradation of the particular analyte an assay is designed to detect. Preferred protease inhibitor concentrations can be empirically determined by spiking the standard with a known concentration of a particular analyte (e.g., an antibody or a ligand), and different concentrations of the protease inhibitor and then determine the loss of activity of the analyte (e.g., loss of binding by the antibody or ligand) over time. Methods of measuring changes in a ligand's binding activity are well known to those of skill. Id. Typically protease inhibitor concentrations will range from about 0.005 g/L to about 0.5 g/L, more preferably from about 0.001 g/L to about 0.1 g/L and most preferably from about 0.03 g/L to about 0.08 g/L. In one embodiment, a protease inhibitor concentration of about 0.05 g/L is particularly preferred.

Amylase is a principle enzymatic component of human oral fluid and is thus frequently present in oral fluid-based diagnostics. Oral fluid-based diagnostic assays must therefore often distinguish, and often quantify, the analyte of interest over a background mixture containing amylase. Therefore in a particularly preferred embodiment, it is desirable to include amylase in the synthetic oral fluid standards of this invention to facilitate investigation of confounding effects amylase may have on oral fluid-based assays. Amylase, when present, is provided in a concentration typical of the naturally occurring oral fluid for which the oral fluid standard is a surrogate. Thus, where oral fluid is expected to be collected from unhealthy subjects, the amylase concentration is adjusted to reflect the amylase concentration associated with the particular subject pathology. Conversely, where the oral fluid standard is intended as a measure of a "healthy" subject, the amylase concentration reflects normal values. In a preferred embodiment, amylase, when present, ranges from about 0.1 g/L to about 5 g/L, more preferably from about 0.2 g/L to about 3 g/L and most preferably from about 0.25 g/L to about 1 g/L.

Other enzymes, preferably types which are present in human oral fluid such as lysozyme, lactoperoxidase, etc. can also be included in the oral fluid standards of this invention.

The synthetic oral fluid standards of this invention can additionally include a preservative. The term "preservative", as used herein, is intended to designate a substance showing antimicrobial properties, in particular bactericidal properties and preferably also antifungal properties. The preservative (or combinations of preservatives) having bactericidal and, preferably, also fungicidal properties may be present in the final composition, or may be included in the preparation of the composition in such a way that it is substantially no longer present in the final composition (having reduced bacterial and/or fungal load of the oral fluid standard).

A wide variety of preservatives can be used with the oral fluid standards of this invention. Suitable preservatives include, but are not limited to peroxides (e.g., hydrogen peroxide), thiocyanate, thimerosal, sodium azide, gentamycin, chlorhexidine gluconate, and polyhexamethylenediguanide. Preferred preservatives have a low toxicity to humans (e.g., $LD_{50}$ greater than about 0.1 g/kg, preferably greater than about 1 g/kg, and most preferably greater than about 2 g/kg in mice when administered orally). Particularly preferred preservatives include, but are not limited to gentamicin, chlorhexidine gluconate, polyhexamethylenediguanide, thimerosal, and the like.

Thiocyanates have a certain antimicrobial activity which is, of course, a desired property in the composition of the invention. Thiocyanate is also a constituent of human natural oral fluid and constitutes part of an antibacterial system comprising thiocyanate, hydrogen peroxide, and lactoperoxidase. When hydrogen peroxide and thiocyanate are present in the composition of the invention, two components of this system are supplied by the composition. The third component of the system, lactoperoxidase, present in natural salivary secretions, can also be added to the oral fluid standards of this invention and thus produce a preservative system that also reflects chemical conditions of natural oral fluid.

In various particular embodiments, the composition of the invention also contains other constituents which are often found in natural oral fluids such as ion species found in human oral fluid, typically one or several ions selected from the group consisting of sodium, potassium, chloride, calcium, iodide, magnesium, phosphate, copper, bicarbonate, nitrate, nitrite, and thiocyanate. One of skill will readily appreciate that ion concentrations of oral fluid vary dramatically with health, physiological state (e.g., fasting or fed), with flow rate of salivary glands, and with relative contribution of different sources of salivary secretions (e.g., parotid, submandibular and sublingual glands). Table 1 provides suitable ranges for as well as particularly preferred ranges for one embodiment.

TABLE 1

Preferred ranges of synthetic salvia standard components.

| Component | Concentration |
| --- | --- |
| Sodium | 2–80 mM |
| Potassium | 10–40 mM |
| Calcium | 0.5–5.0 mM |
| Magnesium | 0.03–0.6 mM |
| Copper | 0.2–12 μM |
| Chloride | 10–56 mM |
| Hydrogen carbonate (bicarbonate) | 2–35 mM |
| Phosphate | 1.8–25 mM |
| Iodide | 0.2–22 μM |
| Bromide | 2.5–22 μM |
| Thiocyanate | 0.4–12.2 μM |
| Hypothiocyanate | 0.6–1.6 μM |
| Nitrate | 0.1–183 μM |
| Nitrite | 0.1–0.2 mM |

In a particularly preferred embodiment, the oral fluid standards of this invention include the following ionic species as shown in Table 2.

TABLE 2

Oral fluid standard ion concentrations in one preferred embodiment.

| Component | Concentration (mM) |
| --- | --- |
| Sodium | 13.7 |
| Potassium | 17.8 |
| Calcium | 1.4 |
| Magnesium | 0.3 |
| Chloride | 37.3 |
| Bicarbonate | 3 |
| Phosphate | 17.8 |
| Nitrite | 0.18 |

The above-identified list of additional components is, of course, not limiting. One of skill will readily appreciate that one or more of the above-identified ionic species can be omitted, additional species can be included, and concentrations of the various ionic species can be altered.

The various ionic components are not added individually to the oral fluid standard, but instead are provided as components of various compounds such as salts. Thus, for example, sodium (Na) can be provided as $NaNO_2$, NaCl, $NaHCO_3$, and the like. Methods of creating buffers having particular ion concentrations are well known to those of skill in the art.

In a preferred embodiment, the synthetic oral fluid standards are prepared by conventional means, typically including the steps of mixing the components of the oral fluid standard at substantially atmospheric pressure, and room temperature so as to form a substantially homogeneous mixture. The mixture can be filtered e.g., through a 0.45 μm porous filter followed by a 0.2 μm microporous filter. It may be necessary to replace filters one or more times if they become clogged during filtration.

After the solution is made it is typically checked for pH and conductivity. The pH preferably ranges from about 5 to about 8, more preferably from about 5.8 to about 7.8, and most preferably is about 6.5±0.2. In a particularly preferred embodiment, the resulting solution is clear and "fresh" and sterile following filtration. It preferably can be stored for more than 12 months at 4° C. in a container from which portions are withdrawn occasionally such as once a day.

The material may be used directly, packaged in any vessel capable of storing aqueous solutions, or frozen for future use. Alternatively, the oral fluid standard can be dehydrated (e.g., lyophilized) for storage as a dry powder which can be reconstituted at a later time by addition of water. As will be understood, the composition, when ready for use, will contain the mucin, and other components when present, in aqueous solution (or, expressed more correctly, in aqueous colloid solution). However, as indicated, it is within the scope of the invention to supply the composition in the form of a dry formulation, e.g., a powder or granulate, for reconstitution before use.

Use of Oral Fluid Standards

The oral fluid standards of this invention can be used for testing, calibrating, or standardizing a wide variety of collection, handling, preservation, and assay formats. In a simple approach, e.g., to test mechanical collection devices, a "minimal standard" can be prepared that consists only of an aqueous solution of a mucin, more preferably an aqueous solution of a mucin and a protease inhibitor and most preferably an aqueous solution of a mucin, a protease inhibitor and an amylase, and approximates the viscosity of oral fluid found in patients expected to be sampled.

Where it is desired to determine how the collection, handling, preservation, and/or nature of the assay affect the detection of one or more particular analytes, the oral fluid standard can additionally include the target analyte(s) to be tested. Of course the oral fluid standard can additionally include any of the other components (e.g., salts, ions, preservatives, etc.) described above.

Virtually any analyte that can be suspended or dissolved in an aqueous solution can be used in the oral fluid standards of this invention. Examples of analytes of interest include 1) antibodies such as antibodies to HIV (e.g., HIV-1 and HIV-2), HTLV (e.g., HTLV-1, HTLV-2), *Helicobacter pylori*, hepatitis (e.g., hepatitis A, B and C), measles, mumps, and rubella; 2) drugs of abuse and their metabolic byproducts such as cotinine, cocaine, benzoylecgonine, benzodizazpine, tetrahydrocannabinol, nicotine, ethanol; 3) therapeutic drugs including theophylline, phenytoin, acetaminophen, lithium, diazepam, nortryptyline, secobarbital, phenobarbitol, theophylline, and the like; 4) hormones and growth factors such as testosterone, estradiol, 17-hydroxyprogesterone, progesterone, thyroxine, thyroid stimulating hormone, follicle stimulating hormone, luteinizing hormone, transforming growth factor alpha, epidermal growth factor, insulin-like growth factor I and II, growth hormone release inhibiting factor, IGA and sex hormone binding globulin; and 5) other analytes including glucose, cholesterol, caffeine, cholesterol, corticosteroid binding globulin, DHEA binding glycoprotein, and the like.

Oral fluid standards spiked with a single analyte of interest are useful for detecting the effect of the oral fluid collection device and/or preservation and subsequent handling steps, and/or assay on the particular analyte or for determining the sensitivity (threshold levels of detection) afforded by particular collection device, handling method, or assay. Often however, oral fluid-based assays require detection of a target analyte from a complex mixture of other biological molecules (e.g., other antibodies, serum proteins, etc.) that can occur in oral fluid. The oral fluid standards of this invention can mimic such complex solutions when they are "spiked" with other biological molecules in addition to the target analyte. The oral fluid standards can be spiked with relatively simple components (e.g., Just a single species such as a protein, enzyme, or particular analyte) or relatively complex combinations of biological molecules such as whole blood or various fractionated blood components (e.g., blood plasma, blood serum, etc.). Negative controls can be prepared by spiking the oral fluid standard, as indicated above, with all the components except the target analyte. Conversely, positive oral fluid standards will include the target analyte.

In a particularly preferred embodiment, the oral fluid standards of this invention are spiked with serum that is either negative (to produce a negative control) or positive (to produce a test standard) for the analyte of interest. Thus, where oral fluid standards for HIV are to be prepared, the oral fluid standard is spiked with either human serum that is negative for HIV (negative control) or human serum that has tested positive for HIV (test sample).

Calculation of quantities and dilution of analytes is according to standard methods known to those of skill in the art. The desired analyte concentration is typically predetermined and the oral fluid standard dilution, or series of serial dilutions, is then determined appropriately. Samples of such calculations are provided in Examples 1 through 4, below.

As indicated above, the oral fluid standards are useful for calibrating and standardizing oral fluid collection methods, devices and assays. The oral fluid standards of this invention are particularly useful for calibrating and standardizing assays (e.g., immunoassays) for a preselected target analyte. The oral fluid standards are suitable for testing virtually any assay compatible with aqueous solutions, more preferably compatible with oral fluid and oral fluid-like aqueous solutions. Such assays include but are not limited to immunoassays, various ligand binding assays, chemical detection systems, and the like.

Typically the oral fluid standards are used for optimization, and calibration of known assay formats (e.g., sandwich assays, hapten inhibition assays, etc.). Methods of performing such assays are well known to those of skill in the art (see, e.g., U.S. Pat. Nos. 4,366,241, 4,376,110, 4,517,288, and 4,837,168; *Methods in Cell Biology* Volume 37: *Antibodies in Cell Biology*, Asai, ed. Academic Press, Inc. New York (1993); and *Basic and Clinical Immunology* 7th Edition, Stites & Terr, eds. (1991)). It will also be appreciated however, that the oral fluid standards are useful for the development and testing of currently unknown collection, handling preservation and assay systems and it will be recognized that the oral fluid standards of this invention can be used in any ex vivo application requiting oral fluid or an oral fluid-like substance.

EXAMPLES

The following examples are offered to illustrate, but not to limit the present invention.

Example 1

Preparation of Substitute Oral Fluid Standard Base

To make the substitute oral fluid standard of this invention, a 5% mucin solution was first prepared by adding 200 ml. of deionized water to 10 g. of mucin and stirring the mixture until all the mucin was dissolved. Then the following ingredients were mixed in the order listed in about 800 ml of deionized water while stirring.

| Ingredients | mM/L | FW | g/L |
|---|---|---|---|
| $NaNO_2$ | 0.18 | 69.0 | 0.01 |
| $MgCl_2$ | 0.30 | 95.22 | 0.03 |
| $CaCl_2 \cdot 2H_2O$ | 1.40 | 147.02 | 0.21 |
| NaCl | 10.5 | 58.44 | 0.61 |
| $KH_2PO_4$ | 12.0 | 136.09 | 1.63 |
| $K_2HPO_4$ | 2.90 | 174.2 | 0.50 |
| KCl | 13.4 | 74.55 | 1.00 |
| $NaHCO_3$ | 3.00 | 84.01 | 0.25 |
| Thimerosol | 0.02% | 404.8 | 0.20 |
| Amylase | | | 0.725 |
| Mucin (5%) | | | 2.0 ml |
| Antipain | 50 µg/ml | 604.7 | 0.05 |

After all the ingredients were dissolved, deionized water was added to make 1 liter and mixed thoroughly. The total amount of water to make 1 liter is about 998 ml. All the mixing may be at room temperature. It will be appreciated that it is not necessary to prepare 1 liter at a time. A batch may be made which is enough for immediate use, or a large amount may be made and frozen in aliquots of a predetermined size.

After the solution was made, a 25 ml. sample was removed and pH and conductivity measured. The pH should typically be 6.5±0.2. However, the pH can range from about 5.8 to about 7.8.

The solution was filtered once through 0.45 µm commercially available microporous filters and then passed through 0.2 μm microporous filters. Due to the viscous nature of the solution, filters became clogged so it was necessary to change filters often. A total of 10 filters were used in the first filtration step and two filters in the second. The solution was be stored at 4° C. until used.

Example 2

Evaluation of HIV-1 Positive and HIV-1 Negative Serum

HIV-1 negative serum is titrated into substitute oral fluid standard base and tested in IgG EIA to determine the level of dilution necessary to obtain the target IgG level of 8–12 μg/ml.

The HIV-1 positive serum is titrated into substitute oral fluid standard base as tested using the Vironostika® HIV-1 Microelisa System made by Organon Teknika. The suggested starting point is a 1:200 dilution for a titration series of 11 dilutions. The proper total dilution is chosen taking into account the dilution when the substitute oral fluid standard is ultimately added to any preservative in the collection device used. For instance when using the OraSure® collection system of Epitope, Inc., the dilution with preservative solution would be 1:3 (oral fluid standard:preservative).

Using the negative serum dilution which is determined and the proper positive serum total dilution, the predilution of the positive serum is calculated.

Example 3

Formulation of Substitute Oral fluid Standard HIV-1 Positive

The following calculations are first completed:

1. Total volume of serum to spike is calculated as $$TV=1/y \times PBV$$

where 1/y is the predetermined dilution of the positive or negative analyte; PBV is the planned batch volume (ml); and TV is the total volume of serum to spike (ml).

2. Predilution volume of high positive serum is calculated as:

$$1/y \times TV = HP$$

where 1/y is as defined above; TV is as defined above; and HP is the volume of high positive serum.

3. Negative serum volume is calculated as:

$$TV - HP = NS$$

where TV is as defined above; Hp is as defined above; and NS is the volume of negative serum.

The planned batch volume of substitute oral fluid standard base is measured and placed in a sterile container. A volume of substitute-oral fluid standard base equal to TV is removed from the sterile container. The volume of high positive serum (HP) calculated above is added, the volume of negative serum (NS) calculated above is added and then mixed thoroughly. The solution is stored at 4° C. until needed.

Example 4

Formulation of Substitute Oral Fluid Standard HIV-1 Negative

The following calculations are first completed:

1. Total volume of serum to spike is calculated as $$1/y \times PBV = TVNS$$

where 1/y is predetermined dilution; PBV is the planned batch volume (ml); and TVNS is the total volume of negative serum to spike (ml).

The planned batch volume of substitute oral fluid standard base is measured and placed in a sterile container. A volume of substitute oral fluid standard base equal to TVNS is removed from the sterile container. The volume of negative serum (TVNS) calculated above is added and then mixed thoroughly. The solution may be stored at 4° C until needed.

Example 5

Simulated Collection

A desired number of collection device packages are opened and treated with the substitute oral fluid standard positive or negative solution. In the case of Epitope, Inc.'s OraSure® collection devices which use absorbent collection pads, the collection pads are placed onto plastic wrap. Then about 400 μl of the substitute oral fluid standard reagent is carefully pipetted onto each pad. The pads are covered by folding the plastic wrap over them to prevent evaporation and held at room temperature for 5 to 30 minutes. The pads are then placed in their respective specimen vials, the handles are snapped off, the vials are capped, and then the vials are incubated at room temperature for at least one hour. The samples are then eluted as described in the aforementioned U.S. Pat. No. 5,103,836). Following elution, the samples are tested using any known HIV-1 ELISA test.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. An oral fluid standard comprising an aqueous solution of a mucin, and a protease inhibitor.

2. The oral fluid standard of claim 1, further comprising an amylase.

3. The oral fluid standard of claim 2, wherein said protease inhibitor inhibits papain-like (cysteine) proteases.

4. The oral fluid standard of claim 3, wherein said protease inhibitor is selected from the group consisting of leupeptin, antipain, benzamidine, chymostatin, pepstatin A, and aprotinin.

5. The oral fluid standard of claim 2, wherein:
   said mucin is present at a concentration ranging from about 0.001% to about 0.4% (w/v);
   said amylase is present at a concentration ranging from about 0.1 g/L to about 5.0 g/L; and
   said protease inhibitor is present in a concentration sufficient to prevent proteolysis of antibodies added to said oral fluid standard.

6. The oral fluid standard of claim 2, further comprising one or more compounds selected from the group consisting of magnesium, calcium, sodium, phosphate, chloride, potassium, and bicarbonate.

7. The oral fluid standard of claim 2, further comprising a preservative.

8. The oral fluid standard of claim 7, wherein said preservative is selected from the group consisting of thimerosal, gentamyin, chlorhexidine gluconate, and polyhexamethylenediguanide.

9. The oral fluid standard of claim 2, further comprising an analyte.

10. The oral fluid standard of claim 2, further comprising human serum.

11. The oral fluid standard of claim 10, wherein a preselected analyte is present in said human serum.

12. The oral fluid standard of claim 11, wherein said preselected analyte is an antibody selected from the group consisting of an antibody specific to HIV-1, an antibody specific to HIV-2, an antibody specific to HTLV-1, an antibody specific to HTLV-2, an antibody specific to *Helicobacter pylori*, an antibody specific to hepatitis A, an antibody specific to hepatitis B, an antibody specific to hepatitis C, an antibody specific to measles, an antibody specific to mumps, an antibody specific to rubella, cotinine, cocaine, benzoylecgonine, benzodiazapine, tetrahydrocannabinol, theophylline, phenytoin, β-hCG, thyroxine, thyroid stimulating hormone, follicle stimulating hormone, luteinizing hormone, glucose, insulin, and cholesterol.

13. The oral fluid standard of claim 10, wherein a preselected analyte is absent from said human serum.

14. The oral fluid standard of claim 13, wherein said analyte is an antibody selected from the group consisting of an antibody specific to HIV-1, an antibody specific to HIV-2, an antibody specific to HTLV-1, an antibody specific to HTLV-2, an antibody specific to *Helicobacter pylori*, an antibody specific to hepatitis A, an antibody specific to hepatitis B, an antibody specific to hepatitis C, an antibody specific to measles, an antibody specific to mumps, an antibody specific to rubella, cotinine, cocaine, benzoylecgonine, benzodiazapine, tetrahydrocannabinol, theophylline, phenytoin, β-hCG, thyroxine, thyroid stimulating hormone, follicle stimulating hormone, luteinizing hormone, glucose, insulin, and cholesterol.

15. The oral fluid standard of claim 6, wherein said oral fluid standard comprises:

magnesium at a concentration ranging from about 0.03 mM to about 0.6 mM;

calcium at a concentration ranging from about 0.5 mM to about 5.0 mM;

sodium at a concentration ranging from about 2 mM to about 80 mM;

phosphate at a concentration ranging from about 1.8 mM to about 25 mM;

chloride at a concentration ranging from about 10 mM to about 56 mM;

potassium at a concentration ranging from about 10 mM to about 40 mM; and bicarbonate at a concentration ranging from about 2 mM to about 35 mM;

and further comprises nitrite at a concentration ranging from about 0.1 mM to about 0.2 mM.

16. The oral fluid standard of claim 15, further comprising thimerosal at a concentration ranging from about 0.1 g/L to about 1 g/L.

17. The oral fluid standard of claim 16, wherein said fluid standard comprises:

about 0.01 g/L NaNO$_2$;

about 0.03 g/L MgCl$_2$;

about 0.21 g/L CaCl$_2$.2H$_2$O;

about 0.61 g/L NaCl;

about 1.63 g/L KH$_2$PO$_4$;

about 1.00 g/L KCl;

about 0.25 g/L NaHCO$_3$;

about 0.20 g/L thimerosal;

about 0.725 g/L amylase;

about 2.0 ml of a 5 % solution of mucin; and about 0.05 g/L antipain.

18. A method of evaluating an assay for the detection of an analyte in oral fluid, said method comprising:

providing an oral fluid standard comprising an aqueous solution of:
a mucin;
a protease inhibitor; and
said analyte;

performing said assay to detect said analyte in said oral fluid standard.

19. The method of claim 18, wherein said oral fluid standard further comprises an amylase.

20. The method of claim 19, wherein said analyte is selected from the group consisting of an antibody specific to HIV-1, an antibody specific to HIV-2, an antibody specific to HTLV-1, an antibody specific to HTLV-2, an antibody specific to *Helicobacter pylori*, an antibody specific to hepatitis A, an antibody specific to hepatitis B, an antibody specific to hepatitis C, an antibody specific to measles, an antibody specific to mumps, an antibody specific to rubella, cotinine, cocaine, benzoylecgonine, benzodiazapine, tetrahydrocannabinol, theophylline, phenytoin, β-hCG, thyroxine, thyroid stimulating hormone, follicle stimulating hormone, luteinizing hormone, glucose, insulin, and cholesterol.

21. The method of claim 20, wherein said assay is an immunoassay.

22. The method of claim 21, wherein said immunoassay is an ELISA.

23. The method of claim 19, wherein said mucin is present at a concentration ranging from about 0.001% to about 0.4% (w/v);

said amylase is present at a concentration ranging from about 0.1 g/L to about 1.0 g/L; and said protease inhibitor is present in a concentration sufficient to prevent proteolysis of antibodies added to said oral fluid standard.

24. The method of claim 19, wherein said protease inhibitor inhibits papain-like (cysteine) proteases.

25. The method of claim 19, wherein said protease inhibitor is selected from the group consisting of leupeptin, antipain, benzamidine, chymostatin, pepstatin A, and aprotinin.

26. The method of claim 19, wherein said oral fluid standard further comprises one or more compounds selected from the group consisting of magnesium, calcium, sodium, phosphate, chloride, potassium, and bicarbonate.

27. The method of claim 19, further comprising a preservative.

28. The method of claim 27, wherein said preservative is selected from the group consisting of thimerosal, gentamyin, chlorhexidine gluconate, and polyhexamethylenediguanide.

29. The method of claim 19, wherein said oral fluid standard further comprises human serum.

30. The method of claim 29, wherein a preselected analyte is present in said human serum.

31. The method of claim 30, wherein said analyte is an antibody selected from the group consisting of an antibody specific to HIV-1, an antibody specific to HIV-2, an antibody specific to HTLV-1, an antibody specific to HTLV-2, an antibody specific to *Helicobacter pylori*, an antibody specific to hepatitis A, an antibody specific to hepatitis B, an antibody specific to hepatitis C, an antibody specific to measles, an antibody specific to mumps, an antibody specific to rubella, cotinine, cocaine, benzoylecgonine, benzodiazapine, tetrahydrocannabinol, theophylline, phenytoin, β-hCG, thyroxine, thyroid stimulating hormone, follicle stimulating hormone, luteinizing hormone, glucose, insulin, and cholesterol.

32. The method of claim 29, wherein a preselected analyte is absent from said human serum.

33. The method of claim 32, wherein said analyte is an antibody selected from the group consisting of an antibody specific to HIV-1, an antibody specific to HIV-2, an antibody specific to HTLIV-1, an antibody specific to HTLV-2, an antibody specific to *Helicobacter pylori*, an antibody specific to hepatitis A, an antibody specific to hepatitis B, an antibody specific to hepatitis C, an antibody specific to measles, an antibody specific to mumps, an antibody specific to rubella, cotinine, cocaine, benzoylecgonine, benzodiazapine, tetrahydrocannabinol, theophylline, phenytoin, β-hCG, thyroxine, thyroid stimulating hormone, follicle stimulating hormone, luteinizing hormone, glucose, insulin, and cholesterol.

34. The method of claim 26, wherein said oral fluid standard further comprises:

nitrite at a concentration ranging from about 0.1 mM to about 0.2 mM;

magnesium at a concentration ranging from about 0.03 mM to about 0.6 mM;

calcium at a concentration ranging from about 0.5 mM to about 5.0 mM;

sodium at a concentration ranging from about 2 mM to about 80 mM;

phosphate at a concentration ranging from about 1.8 mM to about 25 mM;

chloride at a concentration ranging from about 10 mM to about 56 mM;

potassium at a concentration ranging from about 10 mM to about 40 mM; and bicarbonate at a concentration ranging from about 2 mM to about 35 mM.

35. The method of claim 34, wherein said oral fluid standard further comprises thimerosal at a concentration ranging from about 0.1 g/L to about 1 g/L.

36. The method of claim 35, wherein said oral fluid standard comprises:

about 0.01 g/L NaNO$_2$;

about 0.03 g/L MgCl$_2$;

about 0.21 g/L CaCl$_2$.2H$_2$O:

about 0.61 g/L NaCl;

about 1.63 g/L KH$_2$PO$_4$;

about 1.00 g/L KCl;

about 0.25 g/L NaHCO$_3$;

about 0.20 g/L thimerosal;

about 0.725 g/L amylase;

about 2.0 ml of a 5 % solution of mucin; and about 0.05 g/L antipain.

* * * * *

UNITED STATES PATENT AND TRADEMARK OFFICE
CERTIFICATE OF CORRECTION

PATENT NO. : 5,736,322

DATED : April 7, 1998

INVENTOR(S) : Andrew S. GOLDSTEIN

It is certified that error appears in the above-identified patent and that said Letters Patent is hereby corrected as shown below:

In the claims:

In column 12, line 66 (claim 8), please change "gentamyin" to --gentamicin--.
In column 14, line 55 (claim 28), please change "gentamyin" to --gentamicin--.
In column 15, line 12 (claim 32), please change "HTLIV-1" to --HTLV-1--.

Signed and Sealed this

Eighth Day of September, 1998

Attest:

BRUCE LEHMAN

Attesting Officer

Commissioner of Patents and Trademarks